United States Patent [19]
Hawkins

[11] Patent Number: 6,118,016
[45] Date of Patent: Sep. 12, 2000

[54] PROCESS FOR PREPARING PHENOXYPHENYLSULFONYL HALIDES

[75] Inventor: Joel M. Hawkins, Old Lyme, Conn.

[73] Assignee: Pfizer Inc., New York, N.Y.

[21] Appl. No.: 09/287,930

[22] Filed: Apr. 7, 1999

Related U.S. Application Data

[60] Provisional application No. 60/081,393, Apr. 10, 1998.

[51] Int. Cl.$^7$ ............... C07C 301/00; C07C 315/00; C07C 309/00
[52] U.S. Cl. ............ 558/59; 558/60; 568/32; 568/33; 568/34; 568/35; 568/28; 562/30; 562/45; 562/82; 562/83
[58] Field of Search ............... 568/28, 22, 33, 568/35, 34; 562/30, 45, 82, 83; 558/60, 59

[56] References Cited

U.S. PATENT DOCUMENTS 4,745,124  5/1988  Ryan et al. .

FOREIGN PATENT DOCUMENTS

| 0895988 | 2/1999 | European Pat. Off. . |
| 844004 | 10/1951 | Germany . |
| WO91/10644 | 7/1991 | WIPO . |
| WO9325640 | 12/1993 | WIPO . |
| WO96/27583A | 9/1996 | WIPO . |
| WO98/07697A | 2/1998 | WIPO . |
| WO98/33768 | 8/1998 | WIPO . |
| WO9850348 | 11/1998 | WIPO . |
| WO99/07675 | 2/1999 | WIPO . |
| WO99/52910 | 10/1999 | WIPO . |

OTHER PUBLICATIONS

J Amer Chem Soc by Suter vol. 53 No. 3, pp 1112–1116, Mar. 1931.

CA:115:114081 abs of J Chem Soc Perkin Trans 2(7) pp 1071–5 by Chen, 1991.

E. Lee, et al. "Azacycle Synthesis via Radical Cyclization of beta Aminocrylates" *Tetrahedron Letters*, vol. 36 No. 3, Jan. 16, 1995 pp. 417–420.

Montserrat Faja, et al., "Reaction of Uridines and Thymidines with Methyl Propynoate. A New N–3 Protecting Group" *Tetrahedron Letters*, vol. 36, No. 18, pp. 3621–3264, 1995.

Tamejiro Hiyama, et al., "A New Synthesis of 3–amino–2–alkenoates. Novel Synthetic Route to Amino Sugars N–Benzoyl–L–daunosamine and L–acosamine" *Bull. Chem. Soc. Jpn.* 60, pp. 2127–2137 (Jun. 1987).

Theodora W. Greene, et al., "Protective Groups In Organic Synthesis", $2^{nd}$ edition, pp. 250–252, John Wiley & Sons, New York, 1991.

*Primary Examiner*—Paul J. Killos
*Assistant Examiner*—J. Parsa
*Attorney, Agent, or Firm*—Peter C. Richardson; Paul H. Ginsburg; E. Victor Donahue

[57] ABSTRACT

A process for preparing phenoxyphenylsulfonyl halides, which are useful intermediates for the preparation of matrix metalloproteinase inhibitors.

14 Claims, No Drawings

PROCESS FOR PREPARING PHENOXYPHENYLSULFONYL HALIDES

The present application claims priority under 35 USC section 119(e) to U.S. provisional application Ser. No. 60/081,393 filed Apr. 10, 1998, the complete disclosure of which is incorporated by reference as if fully set forth herein.

BACKGROUND OF THE INVENTION

The present invention relates to a process for preparing phenoxyphenylsulfonyl halides, which are useful intermediates for the preparation of matrix metalloproteinase inhibitors and to intermediates thereof.

Inhibitors of matrix metalloproteinase (MMP) are known to be useful for the treatment of a condition selected from the group consisting of arthritis (including osteoarthritis and rheumatoid arthritis), inflammatory bowel disease, Crohn's disease, emphysema, acute respiratory distress syndrome, asthma, chronic obstructive pulmonary disease, Alzheimer's disease, organ transplant toxicity, cachexia, allergic reactions, allergic contact hypersensitivity, cancer, tissue ulceration, restenosis, periodontal disease, epidermolysis bullosa, osteoporosis, loosening of artificial joint implants, atherosclerosis (including atherosclerotic plaque rupture), aortic aneurysm (including abdominal aortic aneurysm and brain aortic aneurysm), congestive heart failure, myocardial infarction, stroke, cerebral ischemia, head trauma, spinal cord injury, neuro-degenerative disorders (acute and chronic), autoimmune disorders, Huntington's disease, Parkinson's disease, migraine, depression, peripheral neuropathy, pain, cerebral amyloid angiopathy, nootropic or cognition enhancement, amyotrophic lateral sclerosis, multiple sclerosis, ocular angiogenesis, corneal injury, macular degeneration, abnormal wound healing, burns, diabetes, tumor invasion, tumor growth, tumor metastasis, corneal scarring, scleritis, AIDS, sepsis, septic shock and other diseases characterized by inhibition of metalloproteinase or ADAM (including TNF-α) expression. In addition, the products which can be prepared from the compounds and processes of the present invention may be used in combination therapy with standard non-steroidal anti-inflammatory drugs (hereinafter NSAID'S), COX-2 inhibitors and analgesics for the treatment of arthritis, and in combination with cytotoxic drugs such as adriamycin, daunomycin, cis-platinum, etoposide, taxol, taxotere and alkaloids, such as vincristine, in the treatment of cancer.

Matrix metalloproteinase inhibitors are well known in the literature. Specifically, PCT publication WO 96/33172 published Oct. 24, 1996, refers to cyclic arylsulfonylamino hydroxamic acids that are useful as MMP inhibitors. U.S. Pat. No. 5,672,615, PCT Publication WO 97/20824, PCT Publication WO 98/08825, PCT Publication WO 98/27069, and PCT Publication WO 98/34918, published Aug. 13, 1998, entitled "Arylsulfonyl Hydroxamic Acid Derivatives" all refer to cyclic hydroxamic acids that are useful as MMP inhibitors. PCT Publications WO 96/27583 and WO 98/07697, published Mar. 7, 1996 and Feb. 26, 1998, respectively, refer to arylsulfonyl hydroxamic acids. PCT Publication WO 98/03516, published Jan. 29, 1998 refers to phosphinates with MMP activity. PCT Publication WO 98/34915, published Aug. 13, 1998, entitled "N-Hydroxy-b-Sulfonyl Propionamide Derivatives," refers to propionyl-hydroxamides as useful MMP inhibitors. PCT Publication WO 98/33768, published Aug. 6, 1998, entitled "Arylsulfonylamino Hydroxamic Acid Derivatives," refers to N-unsubstituted arylsulfonylamino hydroxamic acids. PCT Publication WO 98/30566, published Jul. 16, 1998, entitled "Cyclic Sulfone Derivatives," refers to cyclic sulfone hydroxamic acids as MMP inhibitors. U.S. Provisional patent application Ser. No. 60/55208, filed Aug. 8, 1997, refers to biaryl hydroxamic acids as MMP inhibitors. U.S. Provisional patent application Ser. No. 60/55207, filed Aug. 8, 1997, entitled "Aryloxyarylsulfonylamino Hydroxamic Acid Derivatives," refers to aryloxyarylsulfonyl hydroxamic acids as MMP inhibitors. U.S. Provisional patent application Ser. No. 60/62766, filed Oct. 24, 1997, entitled "The Use of MMP-13 Selective Inhibitors For The Treatment of Osteoarthritis and Other MMP Mediated Disorders," refers to the use of MMP-13 selective inhibitors to treat inflammation and other disorders. U.S. Provisional patent application Ser. No. 60/68261, filed Dec. 19, 1997, refers to the use of MMP inhibitors to treat angiogenesis and other disorders. Each of the above referenced publications and applications is hereby incorporated by reference in its entirety.

The present inventors have now discovered a convenient process for preparing (4-fluorophenoxy-phenyl)-sulfonyl chloride in three steps from 4-chloro-sulfonyl chloride.

SUMMARY OF THE INVENTION

The present invention relates to a compound of the formula

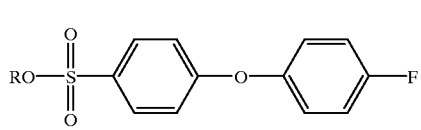

IIa wherein R is H, Li, Na, K, Mg, or NH$_4$, preferably Na, K. or Mg, most preferably Na.

Other preferred compounds of the invention include compounds of the formula

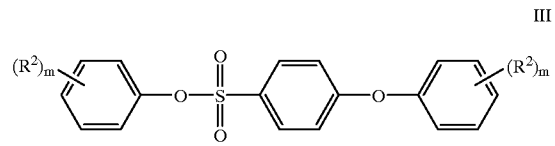

III wherein m is an interger from 1–3;

wherein $R^2$ is fluoro, chloro, bromo, ($C_1$–$C_6$)alkyl, ($C_1$–$C_6$)alkoxy or perfluoro($C_1$–$C_3$)alkyl, preferably fluoro, most preferably wherein $R^2$ is in the 4-position of the phenyl ring.

The present invention also relates to a process for preparing a compound of the formula

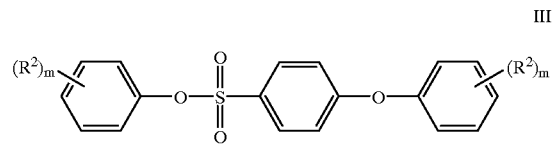

III wherein m is an interger from 1–3;

wherein $R^2$ is fluoro, chloro, bromo, ($C_1$–$C_6$)alkyl, ($C_1$–$C_6$)alkoxy or perfluoro($C_1$–$C_3$)alkyl;

comprising, reacting a compound of the formula

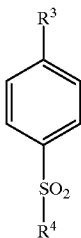

IV wherein $R^3$ is fluoro, chloro or bromo; and $R^4$ is chloro or bromo;
with a compound of the formula

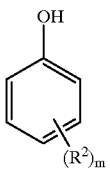

V wherein m is an interger from 1–3, and $R^2$ is fluoro, chloro, bromo, $(C_1-C_6)$alkyl, $(C_1-C_6)$alkoxy or perfluoro $(C_1-C_3)$alkyl;

in the presence of a base, preferably potassium t-butoxide, and a solvent, preferably N-methylpyrrolidinone, at a temperature from 0° C. to about 150° C.

The present invention also relates to a process comprising, reacting said compound of formula III with a base, preferably sodium hydroxide, in a solvent, preferably ethanol, at a temperature from about 50° C. to about 100° C. to form a compound of the formula

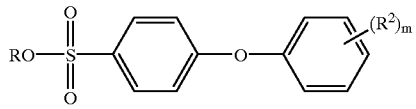

II wherein R is H, Li, Na, K or $NH_4$, preferably Na, K or Mg, most preferably Na;
m is an interger from 1–3; and
$R^2$ is fluoro, chloro, bromo, $(C_1-C_6)$alkyl, $(C_1-C_6)$alkoxy or perfluoro$(C_1-C_3)$alkyl.

The present invention also relates to a process comprising reacting a compound of the formula

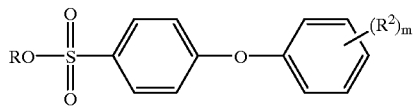

II wherein m is an interger from 1–3;
R is H, Li, Na, K or $NH_4$, preferably Na, K, or Mg, most preferably Na; and $R^2$ is fluoro, chloro, bromo, $(C_1-C_6)$alkyl, $(C_1-C_6)$alkoxy or perfluoro$(C_1-C_3)$alkyl;

with a halogenating agent, preferably thionyl chloride, in a solvent at a temperature from about 0° C. to about 80° C. to form a compound of the formula

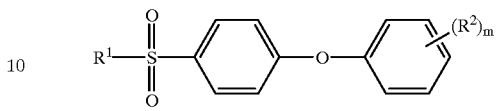

I wherein m is an interger from 1–3;
$R^1$ is halo, preferably chloro, and $R^2$ is fluoro, chloro, bromo, $(C_1-C_6)$alkyl, $(C_1-C_6)$alkoxy or perfluoro$(C_1-C_3)$alkyl, preferably fluoro, chloro, bromo, more preferably fluoro, most preferably wherein $R^2$ is in the 4-position of the phenyl ring. Preferably, the aforementioned reaction is performed in the presence of a catalyst, preferably dimethylformamide, and a solvent, preferably toluene.

DETAILED DESCRIPTION

The following reaction Schemes illustrate the preparation of the compounds of the present invention. Unless otherwise indicated R, $R^1$, $R^2$, $R^3$ and $R^4$ in the reaction Schemes and the discussion that follow are defined as above.

SCHEME 1

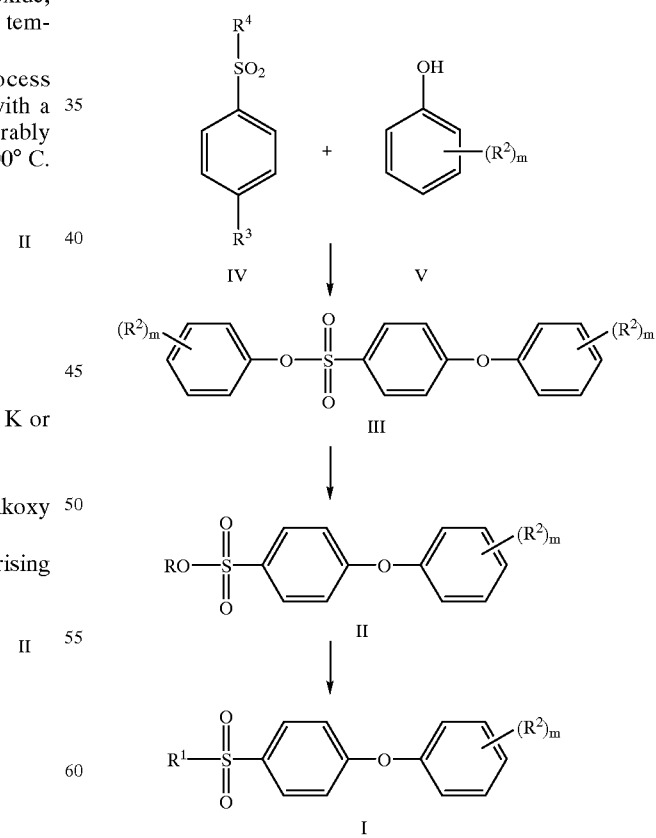

SCHEME 2

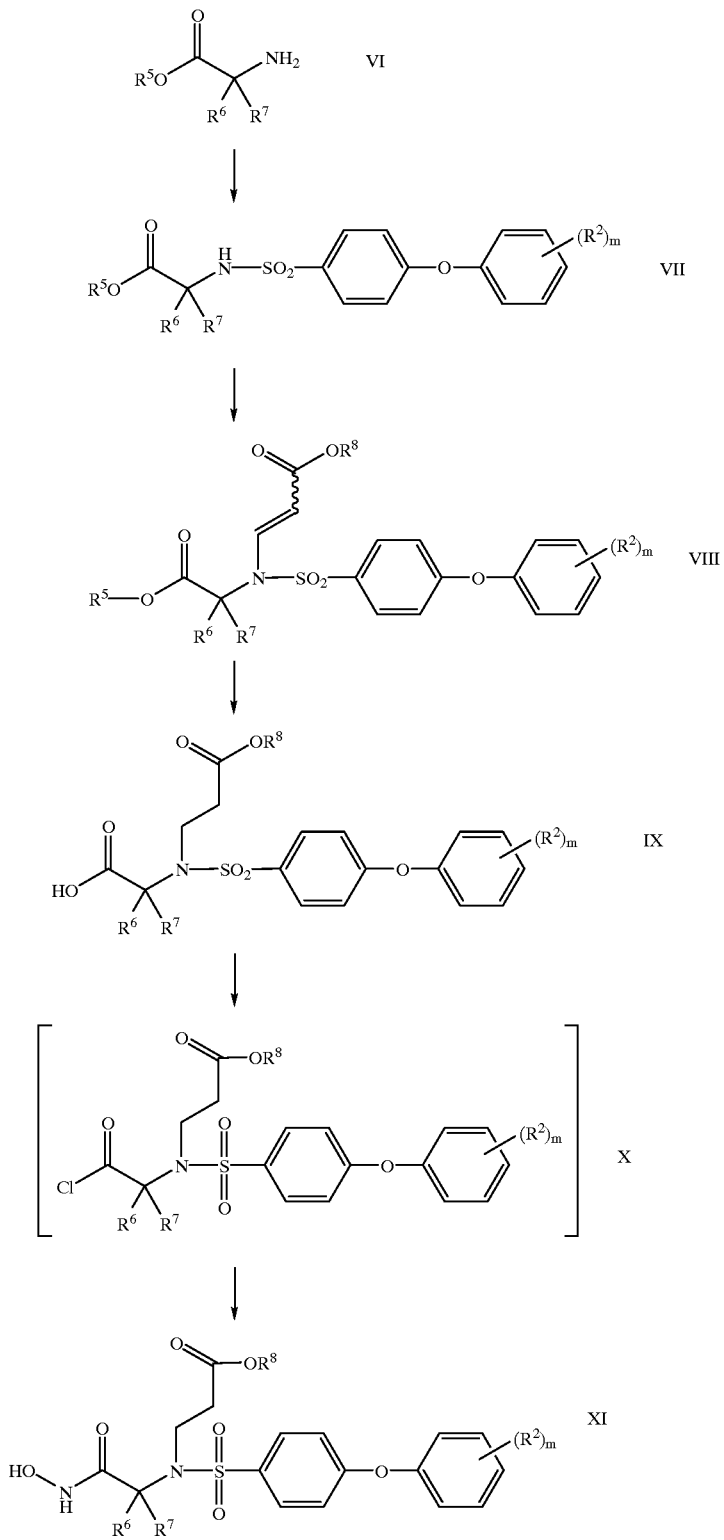

Scheme 1 refers to the preparation of compounds of formula I, wherein $R^1$ is halo. Compounds of the formula I are useful intermediates that can be converted into matrix metalloproteinase inhibitors of formula XI according to the methods of Scheme 2.

Referring to Scheme 1, a compound of the formula I is prepared from a compound of the formula II by reaction with a halogenating agent, preferably in the presence of a solvent and a catalyst. Suitable halogenating agents include oxalyl chloride, thionyl chloride, phosphorous oxychloride or phosphorous pentachloride, preferably thionyl chloride. Suitable catalysts include dimethylformamide. Suitable solvents include toluene, methylene chloride or hexane, preferably toluene. The aforesaid reaction is performed at a temperature of about 0° C. to about 70° C., preferably ranging between 25° C. and about 60° C.

Compounds of the formula II, wherein R is hydrogen, sodium, potassium or ammonium (i.e. H, Li, Na, K or $NH_4$), preferably sodium, can be prepared from compounds of the formula III by reaction with a base in a solvent. One of ordinary skill in the art will understand that when R is Li, Na, K or $NH_4$, the compound of formula II is ionic, and the group R possesses a positive charge, and the adjacent oxygen atom possesses a negative charge. Suitable bases include sodium hydroxide, potassium hydroxide or ammonium hydroxide, preferably sodium hydroxide. Suitable solvents include alcohols such as methanol, ethanol, isopropanol, t-butanol or water and mixtures thereof, preferably ethanol. The aforesaid reaction is performed at a temperature of about 0° C. to about 100° C., preferably ranging between 60° C. to about 80° C.

The compound of the formula III can be prepared by reaction of a compound of the formula IV with a compound of formula V in the presence of a base in a solvent. Suitable bases include hindered alkoxide or carbonate bases such as potassium t-butoxide, sodium t-amyl oxide or potassium carbonate, preferably potassium t-butoxide. More preferably, two equivalents of potassium t-butoxide are used. Suitable solvents include N-methyl-pyrrolidinone, dimethyl formamide, dimethylacetamide or diglyme, preferably N-methyl-pyrrolidinone. The aforesaid reaction is performed at a temperature of about 0° C. to about 150° C., preferably ranging between 25° C. and about 130° C. Most preferably the reaction is conducted at a temperature of about 25° C. for about 1 hour and then the temperature is raised to about 130° C. for about 12 hours.

Compounds of the formulae IV and V are commercially available or can be made by methods well known to those of ordinary skill in the art.

Scheme 2 refers to the preparation of matrix metalloproteinase inhibiting compounds of formula XI, wherein $R^6$ and $R^7$ are as defined for corresponding groups $R^2$ and $R^3$ in PCT Publications WO 96/27583 and WO 98/07697, published Mar. 7, 1996 and Feb. 26, 1998, respectively. Compounds of formula VI can be made according to PCT Publications WO 96/27583 and WO 98/07697, published Mar. 7, 1996 and Feb. 26, 1998. These publications are herein incorporated by reference in their entirety.

Referring to Scheme 2, compounds of said formula XI are prepared from compounds of formula IX by reaction with a chlorinating agent such as oxalyl chloride or thionyl chloride, preferably oxalyl chloride, and a catalytic amount, preferably about 2%, of N,N-dimethylformamide in an inert solvent such as methylene chloride or toluene to form an in situ acid chloride of the formula X that is subsequently reacted with in situ formed silylated hydroxylamine. Silylated hydroxylamine formed in situ is prepared by reaction of hydroxylamine hydrochloride or hydroxylamine sulfate, preferably hydroxylamine hydrochloride, with trimethylsilyl chloride in the presence of a base such as pyridine, 2,6-lutidine, or diisopropylethylamine, preferably pyridine solvent. Suitable silylated hydroxylamine formed in situ are selected from O-trimethylsilylhydroxylamine N,O-bistrimethylsilylhydroxylamine or combinations thereof. The reaction is performed at a temperature of about 0° to about 22° C. (i.e., room temperature) for about 1 to about 12 hours, preferably about 1 hour.

Compounds of the formula IX can be prepared from compounds of the formula VII by reduction in a polar solvent. Suitable reducing agents include palladium catalysts such as hydrogen over palladium, hydrogen over palladium on carbon or hydrogen over palladium hydroxide on carbon, preferably hydrogen over palladium on carbon. Suitable solvents include tetrahydrofuran, methanol, ethanol and isopropanol and mixtures thereof, preferably ethanol. The aforesaid reaction is performed at a temperature of about 22° C. (i.e., room temperature) for a period of 1 to 7 days, preferably about 2 days.

Compounds of the formula VIII can be prepared from compounds of the formula VII, wherein $R^5$ is optionally substituted benzyl, by Michael addition to a propiolate ester with a base in a polar solvent. Suitable propiolates are of the formula $H—C\equiv C—CO_2R^8$ wherein $R^8$ is $(C_1–C_6)$alkyl. Suitable bases include tetrabutylammonium fluoride, potassium carbonate, tertiary amines and cesium carbonate, preferably tetrabutylammonium fluoride. Suitable solvents include tetrahydrofuran, acetonitrile, tert-butanol, t-amyl alcohols and N,N-dimethylformamide, preferably tetrahydrofuran. The aforesaid reaction is performed at a temperature of about −10° C. to about 60° C., preferably ranging between 0° C. and about 22° C. (i.e., room temperature). The compounds of formula VIII are obtained as mixtures of geometric isomers about the olefinic double bond; separation of the isomers is not necessary.

Compounds of the formula VII can be prepared by reaction of compounds of the formula VI with compounds of formula I, from Scheme 1, in the presence of a base in a solvent. Suitable bases include triethylamine, diisopropylethylamine, preferably triethylamine. Suitable solvents include toluene, or methylene chloride, preferably toluene.

Final products of the formula XI can also be saponified to the free acid using a base such as sodium hydroxide in a protic solvent such as ethanol, methanol or water or a mixture such as water and ethanol, water and toluene, or water and THF. The preferred solvent system is water and toluene. The reaction is conducted for a period of 30 minutes to 24 hours, preferably about 2 hours.

The compounds of the formula XI which are basic in nature are capable of forming a wide variety of different salts with various inorganic and organic acids. Although such salts must be pharmaceutically acceptable for administration to animals, it is often desirable in practice to initially isolate a compound of the formula XI from the reaction mixture as a pharmaceutically unacceptable salt and then simply convert the latter back to the free base compound by treatment with an alkaline reagent, and subsequently convert the free base to a pharmaceutically acceptable acid addition salt. The acid addition salts of the base compounds of this invention are readily prepared by treating the base compound with a substantially equivalent amount of the chosen mineral or organic acid in an aqueous solvent medium or in a suitable organic solvent such as methanol or ethanol. Upon careful evaporation of the solvent, the desired solid salt is obtained.

The acids which are used to prepare the pharmaceutically acceptable acid addition salts of the base compounds of this invention are those which form non-toxic acid addition salts, i.e., salts containing pharmacologically acceptable anions, such as hydrochloride, hydrobromide, hydroiodide, nitrate, sulfate or bisulfate, phosphate or acid phosphate, acetate, lactate, citrate or acid citrate, tartrate or bitartrate, succinate, maleate, fumarate, gluconate, saccharate, benzoate, methanesulfonate and pamoate [i.e., 1,1'-methylene-bis-(2-hydroxy-3-naphthoate)] salts.

Those compounds of the formula XI which are also acidic in nature, are capable of forming base salts with various pharmacologically acceptable cations. Examples of such salts include the alkali metal or alkaline-earth metal salts and particularly, the sodium and potassium salts. These salts are all prepared by conventional techniques. The chemical bases which are used as reagents to prepare the pharmaceutically acceptable base salts of this invention are those which form non-toxic base salts with the herein described acidic compounds of formula XI. These non-toxic base salts include those derived from such pharmacologically acceptable cations as sodium, potassium, calcium and magnesium, etc. These salts can easily be prepared by treating the corresponding acidic compounds with an aqueous solution containing the desired pharmacologically acceptable cations, and then evaporating the resulting solution to dryness, preferably under reduced pressure. Alternatively, they may also be prepared by mixing lower alkanolic solutions of the acidic compounds and the desired alkali metal alkoxide together, and then evaporating the resulting solution to dryness in the same manner as before. In either case, stoichiometric quantities of reagents are preferably employed in order to ensure completeness of reaction and maximum product yields.

The ability of the compounds of formula XI or their pharmaceutically acceptable salts (hereinafter also referred to as the active compounds) to inhibit matrix metalloproteinases or the production of tumor necrosis factor (TNF) and, consequently, demonstrate their effectiveness for treating diseases characterized by matrix metalloproteinase or the production of tumor necrosis factor can be determined according to in vitro assay tests well known to those of ordinary skill in the art. One example of an assay recognized as demonstrating that the final products produced by the methods of the invention is the following Inhibition of Human Collagenase Assay.

Biological Assay

Inhibition of Human Collagenase (MMP-1)

Human recombinant collagenase is activated with trypsin using the following ratio: 10 $\mu$g trypsin per 100 $\mu$g of collagenase. The trypsin and collagenase are incubated at room temperature for 10 minutes then a five fold excess (50 $\mu$g/10 $\mu$g trypsin) of soybean trypsin inhibitor is added.

10 mM stock solutions of inhibitors are made up in dimethyl sulfoxide and then diluted using the following Scheme:

10 mM→120 $\mu$M→12 $\mu$M→1.2 $\mu$M→0.12 $\mu$M

Twenty-five microliters of each concentration is then added in triplicate to appropriate wells of a 96 well microfluor plate. The final concentration of inhibitor will be a 1:4 dilution after addition of enzyme and substrate. Positive controls (enzyme, no inhibitor) are set up in wells D1–D6 and blanks (no enzyme, no inhibitors) are set in wells D7–D12.

Collagenase is diluted to 400 ng/ml and 25 $\mu$l is then added to appropriate wells of the microfluor plate. Final concentration of collagenase in the assay is 100 ng/ml.

Substrate (DNP-Pro-Cha-Gly-Cys(Me)-His-Ala-Lys(NMA)-NH$_2$) is made as a 5 mM stock in dimethyl sulfoxide and then diluted to 20 mM in assay buffer. The assay is initiated by the addition of 50 $\mu$l substrate per well of the microfluor plate to give a final concentration of 10 $\mu$M.

Fluorescence readings (360 nM excitation, 460 nm emission) were taken at time 0 and then at 20 minute intervals. The assay is conducted at room temperature with a typical assay time of 3 hours.

Fluorescence vs time is then plotted for both the blank and collagenase containing samples (data from triplicate determinations is averaged). A time point that provides a good signal (the blank) and that is on a linear part of the curve (usually around 120 minutes) is chosen to determine IC$_{50}$ values. The zero time is used as a blank for each compound at each concentration and these values are subtracted from the 120 minute data. Data is plotted as inhibitor concentration vs % control (inhibitor fluorescence divided by fluorescence of collagenase alone×100). IC$_{50}$'s are determined from the concentration of inhibitor that gives a signal that is 50% of the control.

If IC$_{50}$'s are reported to be <0.03 $\mu$M then the inhibitors are assayed at concentrations of 0.3 $\mu$M, 0.03 $\mu$M, 0.03 $\mu$M and 0.003 $\mu$M.

The following Examples illustrate the preparation of the compounds of the present invention. Melting points are uncorrected. NMR data are reported in parts per million (d) and are referenced to the deuterium lock signal from the sample solvent (deuteriochloroform unless otherwise specified). Commercial reagents were utilized without further purification. THF refers to tetrahydrofuran. DMF refers to N,N-dimethylformamide. Chromatography refers to column chromatography performed using 32–63 mm silica gel and executed under nitrogen pressure (flash chromatography) conditions. Room or ambient temperature refers to 20–25° C. All non-aqueous reactions were run under a nitrogen atmosphere for convenience and to maximize yields. Concentration at reduced pressure means that a rotary evaporator was used.

EXAMPLE 1

4-(4-Fluorophenoxy)benzenesulfonic Acid 4-Fluorophenyl Ester

A solution of 14.68 g (0.131 mol, 2.0 equivalents) of potassium tert-butoxide in 27 mL of dry N-methylpyrrolidinone was treated with a solution of 15.39 g (0.137 mol, 2.1 equivalents) of 4-fluorophenol in 27 mL of dry N-methylpyrrolidinone at ambient temperature causing a mild exotherm to 45° C. A solution of 13.81 g (0.065 mol) of 4-chlorobenzenesulfonyl chloride in 27 mL of dry N-methylpyrrolidinone was slowly added to the dark reaction mixture causing a mild exotherm to 44° C. The resulting mixture was stirred at room temperature for one hour and then at 130° C. for 11 hours. The cooled reaction mixture was treated with 162 mL of water, seeded with a trace of 4-(4-fluorophenoxy)benzenesulfonic acid 4-fluorophenyl ester, and granulated at room temperature overnight. The resulting solids were filtered yielding 20.24 g (85%) of 4-(4-fluorophenoxy)benzenesulfonic acid 4-fluorophenyl ester.

$^1$H NMR (CDCl$_3$) δ 7.74 (dd, J=7.0, 2.0 Hz, 2H), 7.14–6.97 (m, 10H). mp 78–83° C.

EXAMPLE 2

4-(4-Fluorophenoxy)benzenesulfonic Acid, Sodium Salt

To a slurry of 47.43 g (0.131 mol) of 4-(4-fluorophenoxy)benzenesulfonic acid 4-fluorophenyl ester in 475 mL of ethanol was added 13.09 g (0.327 mol, 2.5 equivalents) of sodium hydroxide pellets. This mixture was heated at reflux for three hours and stirred overnight at room temperature. The resulting solids were filtered yielding 37.16 g (98%) of 4-(4-fluorophenoxy)benzenesulfonic acid, sodium salt.

$^1$H NMR (CD$_3$OD) δ 7.73–7.78 (m, 2H), 7.05–7.13 (m, 2H), 6.99–7.05 (m, 2H), 6.90–6.95 (m, 2H).

EXAMPLE 3

4-(4-Fluorophenoxy)benzenesulfonyl Chloride

To a slurry of 15.0 g (0.052 mol) of 4-(4-fluorophenoxy) benzenesulfonic acid □, sodium salt, in 150 mL of dry toluene was added 11.3 mL (0.155 mol, 3 equivalents) of thionyl chloride and 0.04 mL (0.5 mmol, 0.01 equivalents) of dimethylformamide. The resulting mixture was stirred at room temperature for 48 hours, filtered through diatomaceous earth, and concentrated under reduced pressure to 40 mL. This solution was used without further purification to prepare 1-[4-(4-fluorophenoxy)benzenesulfonylamino] cyclopentanecarboxylic acid benzyl ester.

A 5.0 mL portion of this solution was concentrated to 1.77 g of 4-(4-fluorophenoxy)benzenesulfonyl chloride as an oil, corresponding to a 96% yield.

$^1$H NMR (CDCl$_3$) δ 7.92–7.97 (m, 2H), 7.01–7.13 (m, 6H). A portion of similarly prepared oil was crystallized from hexane, mp 80° C.

PREPARATION 1

3-[[4-(4-FLUOROPHENOXY) BENZENESULFONYL]-(1-HYDROXYCARBAMOYL-CYCLOPENTYL)AMINO]PROPIONIC ACID

A) 1-[4-(4-Fluorophenoxy)benzenesulfonylamino] cyclopentanecarboxylic Acid Benzyl Ester To a mixture of 12.41 g (0.032 mol) of 1-aminocyclopentanecarboxylic acid benzyl ester, toluene-4-sulfonic acid salt (can be prepared according to the methods of U.S. Pat. No. 4,745,124), and 10.0 g (0.035 mol, 1.1 equivalents) of 4-(4-fluorophenoxy)benzenesulfonyl chloride in 113 mL of toluene was added 11.0 mL (0.079 mol, 2.5 equivalents) of triethylamine. The resulting mixture was stirred at ambient temperature overnight, washed with 2N hydrochloric acid (2×100 mL) and brine (100 mL), dried over sodium sulfate, and concentrated to 30 mL. Hexane, 149 mL, was added drop-wise over three hours giving a solid precipitate which was granulated at 0° C. for one hour and filtered yielding 12.59 g (85%) of 1-[4-(4-fluorophenoxy)benzenesulfonylamino]cyclopentanecarboxylic acid benzyl ester.

$^1$H NMR (CDCl$_3$) δ 7.78–7.82 (m, 2H), 7.30–7.39 (m, 5H), 7.06–7.12 (m, 2H), 6.99–7.04 (m, 2H), 6.93–6.97 (m, 2H), 5.15 (s, 1H), 5.02 (s, 2H), 2.04–2.13 (m, 2H), 1.92–1.98 (m, 2H), 1.62–1.69 (m, 4H).

A 4.0 g sample was granulated in a mixture of 4 mL of ethyl acetate and 40 mL of hexanes overnight giving 3.72 g (93% recovery) of 1-[4-(4-fluorophenoxy) benzenesulfonylamino]-cyclopentanecarboxylic acid benzyl ester as light tan solids, mp 97.0–97.5° C.

B) 1-{(2-Ethoxycarbonylvinyl)-[4-(4-fluorophenoxy) benzenesulfonyl]-amino}-cyclopentanecarboxylic Acid Benzyl Ester A solution of 25.0 g (53.2 mmol) of 1-[4-(4-fluorophenoxy)benzenesulfonylamino]-cyclopentanecarboxylic acid benzyl ester and 10.8 mL (106 mmol, 2 equivalents) of ethyl propiolate in 200 mL of dry tetrahydrofuran at 1° C. was treated with 53.2 mL (53.2 mmol, 1 equivalent) of a solution of tetrabutylammonium fluoride in tetrahydrofuran (1M) over 45 minutes. The resulting solution was allowed to warm slowly to ambient temperature and stirred overnight. The tetrahydrofuran was displaced with toluene at reduced pressure, and the toluene solution was washed with water and brine, diluted to 600 mL with toluene, stirred with 90 g of silica gel for three hours, filtered, and concentrated to 25.14 g (83%) of 1-{(2-ethoxycarbonylvinyl)-[4-(4-fluorophenoxy) benzenesulfonyl]amino}-cyclopentanecarboxylic acid benzyl ester as an orange oil. $^1$H NMR (CDCl$_3$) indicated a 1.5:1 trans/cis ratio.

Trans d 7.74–7.78 (m, 2H), 7.72 (d, J=14 Hz, 1H), 7.26–7.36 (m, 5H), 6.96–7.12 (m, 4H), 6.78–6.84 (m, 2H), 5.44 (d, J=14 Hz, 1H), 5.11 (s, 2H), 4.12 (q, J=7.1 Hz, 2H), 2.08–2.43 (m, 4H), 1.63–1.80 (m, 4H), 1.24 (t, J=7.1 Hz, 3H). Cis d 7.68–7.72 (m, 2H), 7.26–7.36 (m, 5H), 6.96–7.12 (m, 4H), 6.86–6.91 (m, 2H), 6.47 (d, J=8.1 Hz, 1H), 5.90 (d, J=8.1 Hz, 1H), 5.11 (s, 2H), 3.93 (q, J=7.2 Hz, 2H), 2.08–2.43 (m, 4H), 1.63–1.80 (m, 4H), 1.17 (t, J=7.2 Hz, 3H).

C) 1-{(2-Ethoxycarbonylethyl)-[4-(4-fluorophenoxy) benzenesulfonyl]-amino}-cyclopentanecarboxylic Acid A solution of 2.50 g (4.4 mmol) of 1-{(2-ethoxycarbonylvinyl)-[4-(4-fluorophenoxy) benzenesulfonyl]amino}cyclopentanecarboxylic acid benzyl ester in 25 mL of ethanol was treated with 2.5 g of 50% water wet 10% palladium on carbon catalyst and shaken under 53 psi of hydrogen for 21 hours. The catalyst was removed by filtration and washed with ethanol (4×25 mL). The filtrate and washings were combined and concentrated under vacuum to 1.74 g (82%) of crude 1-{(2-ethoxycarbonylethyl)-[4-(4-fluorophenoxy) benzenesulfonyl]amino}cyclopentanecarboxylic acid□ as a viscous oil.

$^1$H NMR (CDCl$_3$) δ 7.78–7.82 (m, 2H), 6.94–7.09 (m, 6H), 4.09 (q, J=7.2 Hz, 2H), 3.56–3.60 (m, 2H), 2.75–2.79 (m, 2H), 2.33–2.39 (m, 2H), 1.93–2.03 (m, 2H), 1.69–1.76 (m, 2H), 1.56–1.63 (m, 2H), 1.22 (t, J=7.2 Hz, 3H).

D) 1-{(2-Ethoxycarbonylethyl)-[4-(4-fluorophenoxy) benzenesulfonyl]-amino}-cyclopentanecarboxylic Acid, Dicyclohexylaminium Salt A solution of 3.10 g (6.5 mmol) of crude 1-{(2-ethoxycarbonylethyl)-[4-(4-fluorophenoxy) benzenesulfonyl]amino}cyclopentanecarboxylic acid in 30 mL of ethanol was treated with 1.28 mL (6.5 mmol, 1 equivalent) of dicyclohexylamine at ambient temperature producing solids within five minutes. This mixture was stirred at ambient temperature overnight and then at 0° C. for five hours. White solids were isolated by filtration, washed with 10 mL of cold ethanol, and air dried giving 2.89 g (67%) of 1-{(2-ethoxycarbonylethyl)-[4-(4-fluorophenoxy) benzenesulfonyl]amino}cyclopentanecarboxylic acid, dicyclohexylaminium salt.

$^1$H NMR (CDCl$_3$) δ 7.86–7.91 (m, 2H), 6.99–7.09 (m, 4H), 6.90–6.94 (m, 2H), 5.3 (br s, 2H), 4.07 (q, J=7.1 Hz, 2H), 3.54–3.59 (m, 2H), 2.88–2.95 (m, 4H), 2.31–2.38 (m, 2H), 1.95–2.22 (m, 6H), 1.68–1.77 (m, 6H), 1.53–1.60 (m, 4H), 1.40–1.50 (m, 4H), 1.21 (t, J=7.1 Hz, 3H), 1.14–1.22 (m, 6H). Mp 164.5–165.9° C.

E) 1-{(2-Ethoxycarbonylethyl)-[4-(4-fluorophenoxy) benzenesulfonyl]-amino}-cyclopentanecarboxylic Acid from 1-{(2-Ethoxycarbonylethyl)-[4-(4-fluorophenoxy) benzenesulfonyl]amino}cyclopentanecarboxylic Acid□, Dicyclohexylaminium Salt A solution of 3.0 g (4.5 mmol) of 1-{(2-ethoxycarbonylethyl)-[4-(4-fluorophenoxy)benzenesulfonyl]amino}cyclopentanecarboxylic acid, dicyclohexylaminium salt in 30 mL of dichloromethane was treated with 30 mL of 2N hydrochloric acid at ambient temperature causing immediate precipitation of solids. This mixture was stirred at ambient temperature for three hours. The solids were filtered, the aqueous phase was extracted with dichloromethane, and the combined organic phases were washed with water, dried over sodium sulfate, and concentrated under vacuum to 2.2 g (100%) of 1-{(2-ethoxycarbonylethyl)-[4-(4-fluorophenoxy)benzenesulfonyl]amino}cyclopentanecarboxylic acid as a clear oil.

$^1$H NMR (DMSO-$d_6$) δ 12.68 (bs,1 H), 7.76–7.80 (m, 2H), 7.25–7.31 (m, 2H), 7.16–7.21 (m, 2H), 7.03–7.08 (m, 2H), 4.01 (q, J=7.1 Hz, 2H), 3.48–3.54 (m, 2H), 2.64–2.70 (m, 2H), 2.13–2.21 (m, 2H), 1.90–1.98 (m, 2H), 1.52–1.59 (m, 4H), 1.14 (t, J=7.1 Hz, 3H).

F) 3-{(1-Chlorocarbonylcyclopentyl)-[4-(4-fluorophenoxy)benzene-sulfonyl]amino}propionic Acid Ethyl Ester A solution of 7.26 g (15.1 mmol) of 1-{(2-ethoxycarbonylethyl)-[4-(4-fluorophenoxy)benzenesulfonyl]amino}cyclopentanecarboxylic acid in 73 mL of dichloromethane was treated with 1.4 mL (17 mmol, 1.1 equivalents) of oxalyl chloride and 0.02 mL (0.3 mmol, 0.02 equivalents) of dimethylformamide at ambient temperature, causing some bubbling, and stirred overnight. The resulting solution of 3-{(1-chlorocarbonylcyclopentyl)-[4-(4-fluorophenoxy)benzenesulfonyl]amino}propionic acid ethyl ester was used for the preparation of 3-[[4-(4-fluorophenoxy)benzenesulfonyl]-(1-hydroxycarbamoylcyclopentyl)amino]propionic acid ethyl ester without isolation.

A similarly prepared solution of 3-{(1-chlorocarbonylcyclopentyl)-[4-(4-fluorophenoxy)benzenesulfonyl]amino}propionic acid ethyl ester was concentrated under vacuum to an oil.

$^1$H NMR (CDCl$_3$) δ 7.84–7.87 (m, 2H), 6.97–7.12 (m, 6H), 4.10 (q, J=7.2 Hz, 2H), 3.55–3.59 (m, 2H), 2.68–2.72 (m, 2H), 2.47–2.53 (m, 2H), 1.95–2.02 (m, 2H), 1.71–1.76 (m, 4H), 1.24 (t, J=7.2 Hz, 3H).

G) 3-[[4-(4-Fluorophenoxy)benzenesulfonyl]-(1-hydroxycarbamoylcyclopentyl)amino]propionic Acid Ethyl Ester A solution of 1.37 g (19.7 mmol, 1.3 equivalents) of hydroxylamine hydrochloride in 9.2 mL (114 mmol, 7.5 equivalents) of dry pyridine at 0° C. was treated with 5.8 mL (45 mmol, 3.0 equivalents) of trimethylsilyl chloride, causing white solids to precipitate, and allowed to warm to ambient temperature overnight. This mixture was cooled to 0° C. and treated with a solution of 7.54 g (15.1 mmol) of 3-{(1-chlorocarbonylcyclopentyl)-[4-(4-fluorophenoxy)-benzenesulfonyl]amino}propionic acid ethyl ester in 73 mL of dichloromethane, prepared as described above without isolation, causing an exotherm to 8° C. This mixture was stirred at 0° C. for 30 minutes and at ambient temperature for one hour before treating with 50 mL of 2N aqueous hydrochloric acid and stirring at ambient temperature for one hour. The aqueous phase was extracted with dichloromethane and the combined organic phases were washed with 2N aqueous hydrochloric acid (2×50 mL) and water (50 mL). This solution of 3-[[4-(4-fluorophenoxy)benzenesulfonyl]-(1-hydroxycarbamoylcyclopentyl)amino]propionic acid ethyl ester in dichloromethane was used for the preparation of 3-[[4-(4-fluorophenoxy)benzenesulfonyl]-(1-hydroxycarbamoylcyclopentyl)amino]propionic acid without isolation. An aliquot was concentrated to a foam.

$^1$H NMR (DMSO-$d_6$) δ 10.37 (s, 1H), 8.76 (s, 1H), 7.74–7.79 (m, 2H), 7.24–7.30 (m, 2H), 7.14–7.20 (m, 2H), 7.01–7.05 (m, 2H), 3.99 (q, J=7.1 Hz, 2H), 3.42–3.47 (m, 2H), 2.62–2.67 (m, 2H), 2.16–2.23 (m, 2H), 1.77–1.85 (m, 2H), 1.43–1.52 (m, 4H), 1.13 (t, J=7.1 Hz, 3H).

A similarly prepared solution was concentrated under vacuum to 6.71 g (89%) of 3-[[4-(4-fluorophenoxy)benzenesulfonyl]-(1-hydroxycarbamoylcyclopentyl)amino] propionic acid ethyl ester as a hard dry foam.

H) 3-[[4-(4-Fluorophenoxy)benzenesulfonyl]-(1-hydroxycarbamoylcyclopentyl)amino]propionic Acid A solution of 7.48 g (15.1 mmol) of 3-[[4-(4-fluorophenoxy)benzenesulfonyl]-(1-hydroxycarbamoylcyclopentyl)amino]propionic acid ethyl ester in dichloromethane was concentrated by rotary evaporation with the addition of 75 mL of toluene. This solution was treated with 75 mL of water, cooled to 0° C., and treated with 6.05 g (151 mmol, 10 equivalents) of sodium hydroxide pellets over 10 minutes with vigorous stirring. This mixture was stirred for 15 minutes at 0° C. and warmed to ambient temperature over one hour. The aqueous phase was separated, diluted with 7.5 mL of tetrahydrofuran, cooled to 0° C., and treated with 33 mL of 6N aqueous hydrochloric acid over 20 minutes. This mixture was stirred with 75 mL of ethyl acetate at 0° C. to ambient temperature, and the ethyl acetate phase was separated and washed with water. The ethyl acetate solution was slowly treated with 150 mL of hexanes at ambient temperature causing solids to precipitate, and stirred overnight. Filtration yielded 5.01 g of 3-[[4-(4-fluorophenoxy)benzenesulfonyl]-(1-hydroxycarbamoylcyclopentyl)amino]propionic acid as a white solid (71% yield from 1-{(2-ethoxycarbonylethyl)-[4-(4-fluorophenoxy)benzenesulfonyl]amino}cyclopentanecarboxylic acid).

$^1$H NMR (DMSO-$d_6$) δ 12.32 (s, 1H), 10.43 (s, 1H), 8.80 (s, 1H), 7.82 (d, J=8.6 Hz, 2H), 7.28–7.35 (m, 2H), 7.20–7.26 (m, 2H), 7.08 (d, J=8.9 Hz, 2H), 3.44–3.49 (m, 2H), 2.61–2.66 (m, 2H), 2.24–2.29 (m, 2H), 1.86–1.90 (m, 2H), 1.54–1.55 (m, 4H). mp 162.9–163.5° C. (dec).

What is claimed is:

1. A compound of the formula

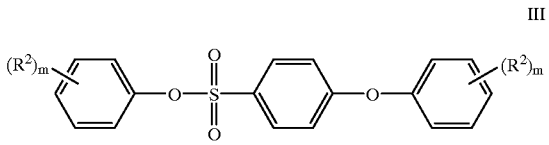

wherein m is an interger from 1–3;

$R^2$ is fluoro, chloro, bromo, $(C_1-C_6)$alkyl, $(C_1-C_6)$alkoxy or perfluoro$(C_1-C_3)$alkyl.

2. A compound according to claim 1 wherein $R^2$ is fluoro.

3. A compound according to claim 2 wherein $R^2$ is in the 4-position of the phenyl ring.

4. A process for preparing a compound of the formula

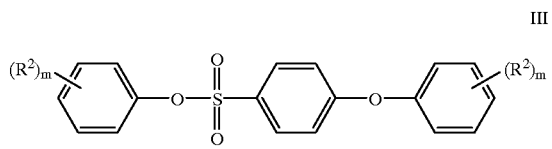

III wherein m is an interger from 1–3;
$R^2$ is fluoro, chloro, bromo, $(C_1-C_6)$alkyl, $(C_1-C_6)$alkoxy or perfluoro$(C_1-C_3)$alkyl;
comprising, reacting a compound of the formula

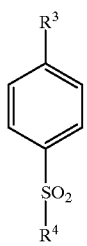

IV wherein $R^3$ is fluoro, chloro or bromo; and
$R^4$ is chloro or bromo;
with a compound of the formula

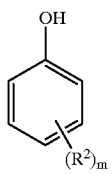

V wherein m is an interger from 1–3; and
$R^2$ is fluoro, chloro, bromo, $(C_1-C_6)$alkyl, $(C_1-C_6)$alkoxy or perfluoro$(C_1-C_3)$alkyl;
in the presence of a base and a solvent at a temperature from 0° C. to about 150° C.

5. A process according to claim 4 wherein said base is potassium t-butoxide and said solvent is N-methylpyrrolidinone.

6. A process according to claim 4 further comprising, reacting said compound of formula III with a base in a solvent at a temperature from about 50° C. to about 100° C. to form a compound of the formula

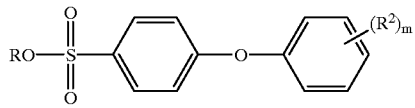

II wherein m is an interger from 1–3;
R is H, Li, Na, K or $NH_4$; and
$R^2$ is fluoro, chloro, bromo, $(C_1-C_6)$alkyl, $(C_1-C_6)$alkoxy or perfluoro$(C_1-C_3)$alkyl.

7. A process according to claim 6 wherein said base is sodium hydroxide and said solvent is ethanol.

8. A process according to claim 6 further comprising reacting a compound of the formula

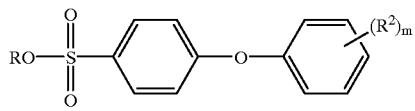

II wherein m is an interger from 1–3;
R is H, Li, Na, K or $NH_4$, and
$R^2$ is fluoro, chloro, bromo, $(C_1-C_6)$alkyl, $(C_1-C_6)$alkoxy or perfluoro$(C_1-C_3)$alkyl;
with a halogenating agent in a solvent at a temperature from about 0° C. to about 80° C. to form a compound of the formula

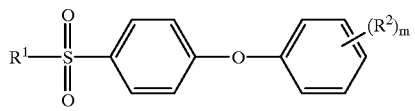

I wherein $R^1$ is halo and m is an integer from 1–3.

9. A process according to claim 8 wherein $R^1$ is chloro.
10. A process according to claim 8 wherein $R^2$ is fluoro.
11. A process according to claim 8 wherein $R^2$ is in the 4-position of the phenyl ring.
12. A process according to claim 8 wherein said halogenating agent is thionyl chloride.
13. A process according to claim 8 further comprising the addition of a catalyst and a solvent.
14. A process according to claim 13 wherein said catalyst is dimethylformamide and said solvent is toluene.

* * * * *